US00PP36934P2

(12) United States Plant Patent
Wu

(10) Patent No.: US PP36,934 P2
(45) Date of Patent: Sep. 2, 2025

(54) BERMUDAGRASS PLANT NAMED 'OSU2081'

(50) Latin Name: ***Cynodon transvaalensis Burtt-Davy* x *Cynodon dactylon Pers.***
Varietal Denomination: OSU2081

(71) Applicant: THE BOARD OF REGENTS FOR THE OKLAHOMA AGRICULTURAL AND MECHANICAL COLLEGES, Stillwater, OK (US)

(72) Inventor: Yanqi Wu, Stillwater, OK (US)

(73) Assignee: THE BOARD OF REGENTS FOR THE OKLAHOMA AGRICULTURAL AND MECHANICAL COLLEGES, Stillwater, OK (US)

( * ) Notice: Subject to any disclaimer, the term of this patent is extended or adjusted under 35 U.S.C. 154(b) by 0 days.

(21) Appl. No.: 18/923,354

(22) Filed: Oct. 22, 2024

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./389
See application file for complete search history.

(56) References Cited

PUBLICATIONS

U.S. Appl. No. 18/923,387, filed Oct. 22, 2024, 14 pages.

*Primary Examiner* — Susan McCormick Ewoldt
(74) *Attorney, Agent, or Firm* — McKee, Voorhees & Sease, PLC

(57) ABSTRACT

'OSU2081' is disclosed as a new clonally propagated F1 hybrid turf bermudagrass cultivar with improved drought resistance, few seed heads, excellent establishment characteristics and green leaf sport resistance. The cultivar exhibits fine leaf texture, high density, dark green color, and sufficient sod tensile strength for large scale commercial production.

5 Drawing Sheets

GOVERNMENT SUPPORT

This invention was made in part with government support under United States Department of Agriculture SCRI Grant Nos. SCRI-2019-1455-05 and 2019-51181-30472 The government has certain rights in this invention.

Botanical designation: Genus and species: *Cynodon transvaalensis* Burtt-Davy x *Cynodon dactylon* Pers.

Cultivar denomination: The new plant has the cultivar denomination 'OSU2081'.

SUMMARY

This disclosure relates to a new and distinct cultivar of bermudagrass designated 'OSU2081' and botanically known as *Cynodon transvaalensis* Burtt-Davy x *Cynodon dactylon* Pers. 'OSU2081' is a new, high-quality, interspecific hybrid turf bermudagrass. It has exhibited a significantly improved drought resistance in a wide range of the southern United States. It has excellent fall color retention and produces few seedheads, which is better than some popular drought-resistant varieties. It has demonstrated excellent establishment characteristics and leaf spot disease resistance, fine leaf texture, high density, dark green color, and sufficient sod tensile strength for reliable, large-scale commercial production on farms.

DETAILED BOTANICAL DESCRIPTION

Description, Origin, and History

Figure 1:
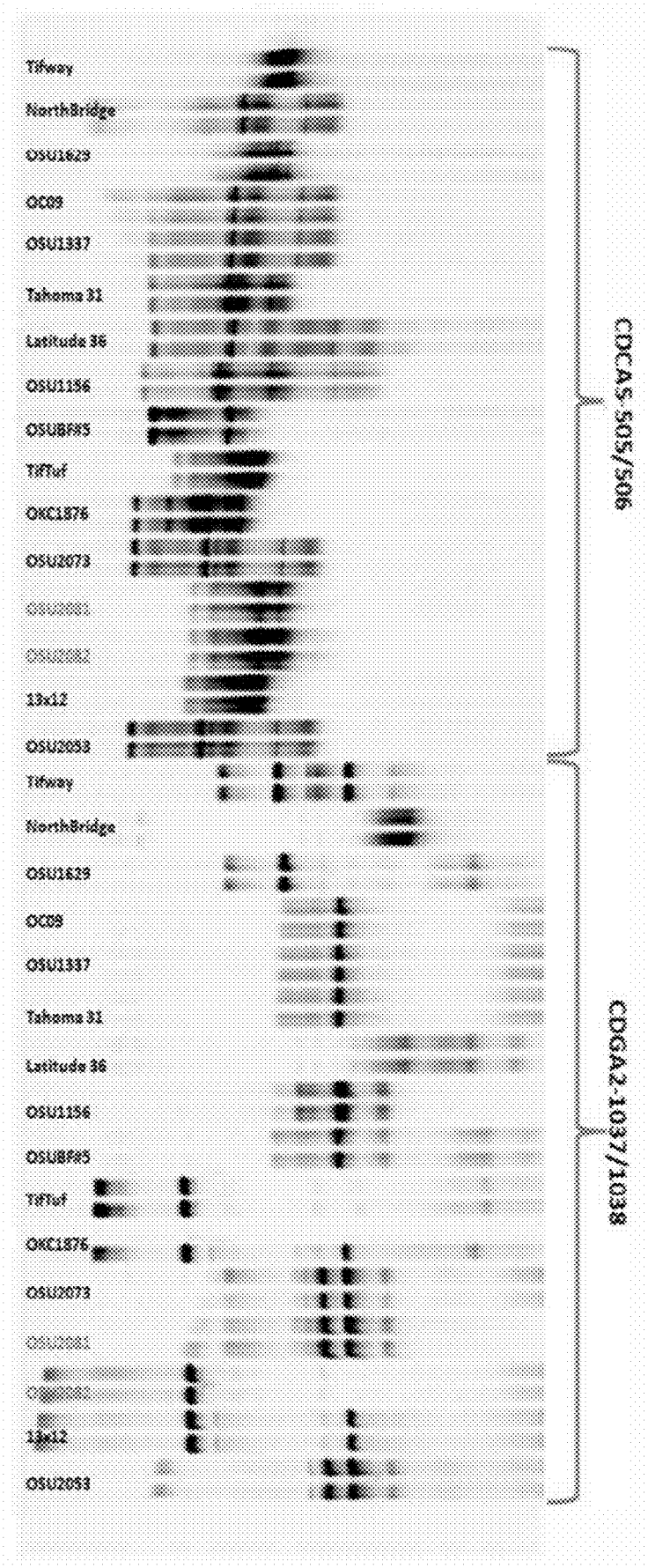
FIG. 1 is a simple sequence repeat DNA band patterns amplified by two primer pairs, CDCA5-505/506 (the gel image on the left) and CDGA2-1037/1038 (on the right) showing 'OSU2081' and 'OSU2082' (U.S. Plant patent application Ser. No. 18/923,387) are distinct genotypes from other entities including 'Tifway', 'NorthBridge', 'Tahoma 31', 'Latitude 36', 'TifTuf' and 'OKC1876'.

'OSU2081' has been vegetatively propagated and is an F1 hybrid derived from a cross between female parent *C. transvaalensis* African bermudagrass selection '2747' (not patented) and male parent *C. dactylon* var. *dactylon* accession 'A10202' (not patented). In 2018, a small crossing plot was established by planting clonal plants of the two parents in proximity in Stillwater, Oklahoma. Mature seedheads were hand-harvested from the African bermudagrass selection ('2747') in the crossing block in summer 2019. Seedlings from the harvested seeds of this cross along with seedlings from other crosses were screened for leaf texture and color, and rooting potential in a greenhouse in Stillwater, Oklahoma in the winter between 2019 and 2020. The hybrid has been included in subsequent multiple tests at Stillwater, Oklahoma, and locations in California, Texas, Georgia, Florida, and North Carolina since 2020. 'OSU2081' is sexually sterile and must be propagated vegetatively. It has been clonally propagated through many seasons in Stillwater, Oklahoma. The cultivar is stable, with advanced generation clonal plants reproducing true to type.

'OSU2081' is sexually sterile, whereas both parents, '2747' and 'A10202', are sexually fertile. 'OSU2081' has leaf blades that are finer than parent 'A10202' but coarser than parent '2747'.

'OSU2081' has a rhizome color of yellowish white (corresponds to RHS 158C, The Royal Horticultural Society Colour Chart, $6^{th}$ edition (2015)); stolon color of moderate yellow green (RHS 145B); upper and lower leaf blade surfaces color (in summer) of strong green (RHS 143A); upper and lower leaf surfaces color (in winter) of strong yellow (RHS 153D); leaf sheath color of light yellowish green (RHS 144D); collar color of greenish white (RHS 157D); and lemma, palea, and culm color of light yellowish green (RHS 145D). 'OSU2081' is sterile so no seed color can be observed.

The rhizome measures 100 mm long and 1.2 mm in diameter on average. The average stolon length and diameter is 250 mm and 1 mm, respectively. The internode length averages 52 mm and internode diameter averages 0.5 mm. The length and width of the leaf blade are 74 mm and 1.97 mm, respectively, on average. The observed length and diameter of leaf sheath are 20 mm and 1 mm, respectively, on average. The observed length of the ligule is 1.3 mm on average. An observed inflorescence has 3 racemes, and each raceme is approximately 35 mm in length. The observed length of the spikelet, glume, palea, lemma, peduncle, and culm is 2.5 mm, 2 mm, 2.5 mm, 2.2 mm, 59 mm, and 110 mm, respectively, on average.

'OSU2081' typically grows laterally with stolons, and vertically and obliquely via stems. This grass can form a dense sod if mowed or trimmed regularly.

'OSU2081' has an acute leaf apex. Its leaf blade margin is smooth. Its leaf blade bears tiny, sparse silver-colored hair on the upper surface while its lower surface is smooth. Its leaf sheath is smooth. 'OSU2081' has a short and hairy ligule. Its auricle is short. Its collar is narrow. Its bud is folded in leaf blades. The inflorescence is digitated with 3 racemes in a whorl. Each raceme bears 18-20 spikelets. One spikelet contains one floret. Typically, 'OSU2081' flowers from late spring to early summer. 'OSU2081' has a purple stigma and is approximately 0.7 mm in length. Its anthers are light yellow and 1.0-1.3 mm long.

DNA Profiling Experiments

Figure 2:
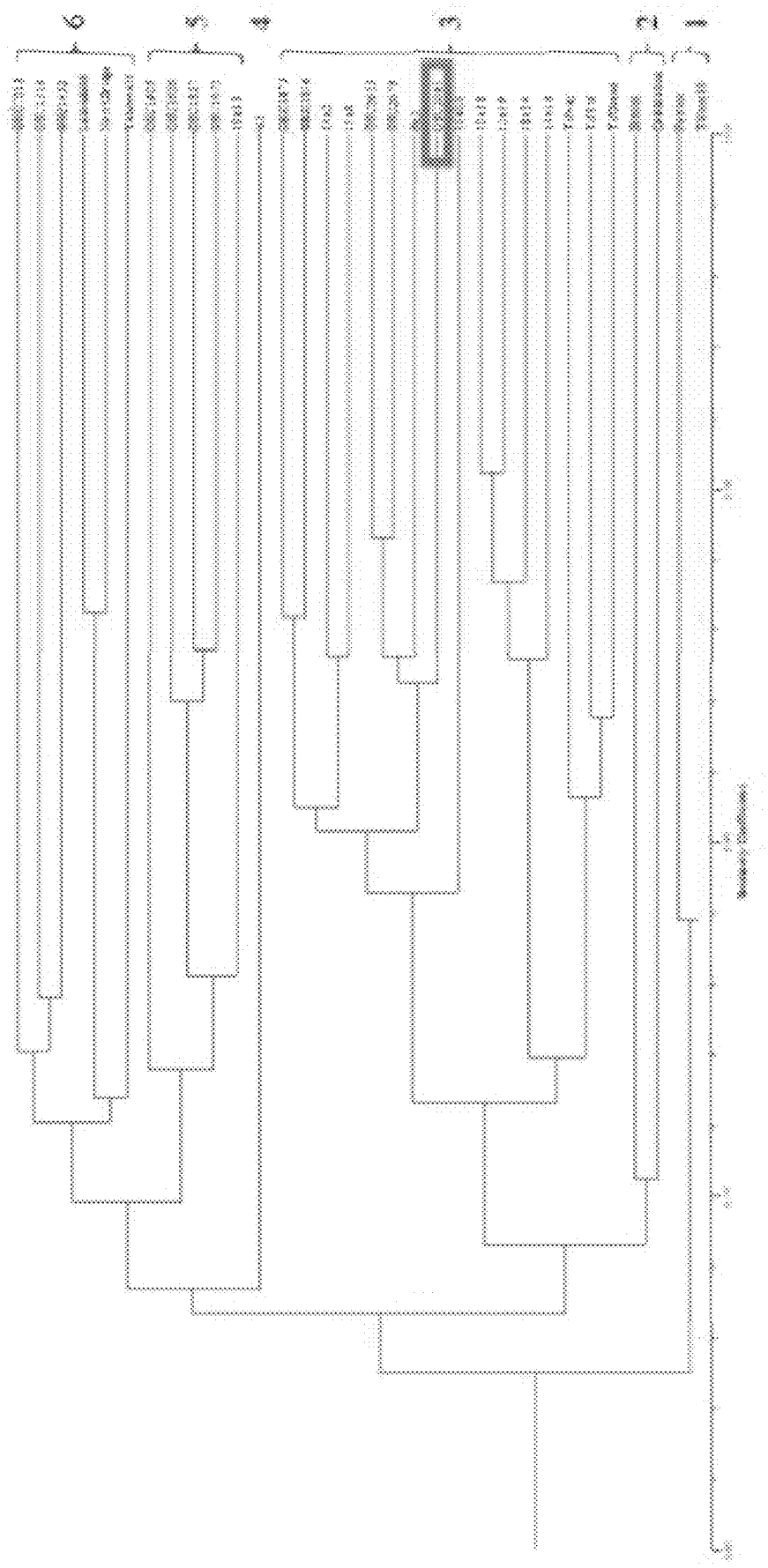
FIG. 2 is a DNA-marker-based dendrogram of 32 bermudagrass genotypes including 'OSU2081'.
Figure 3:
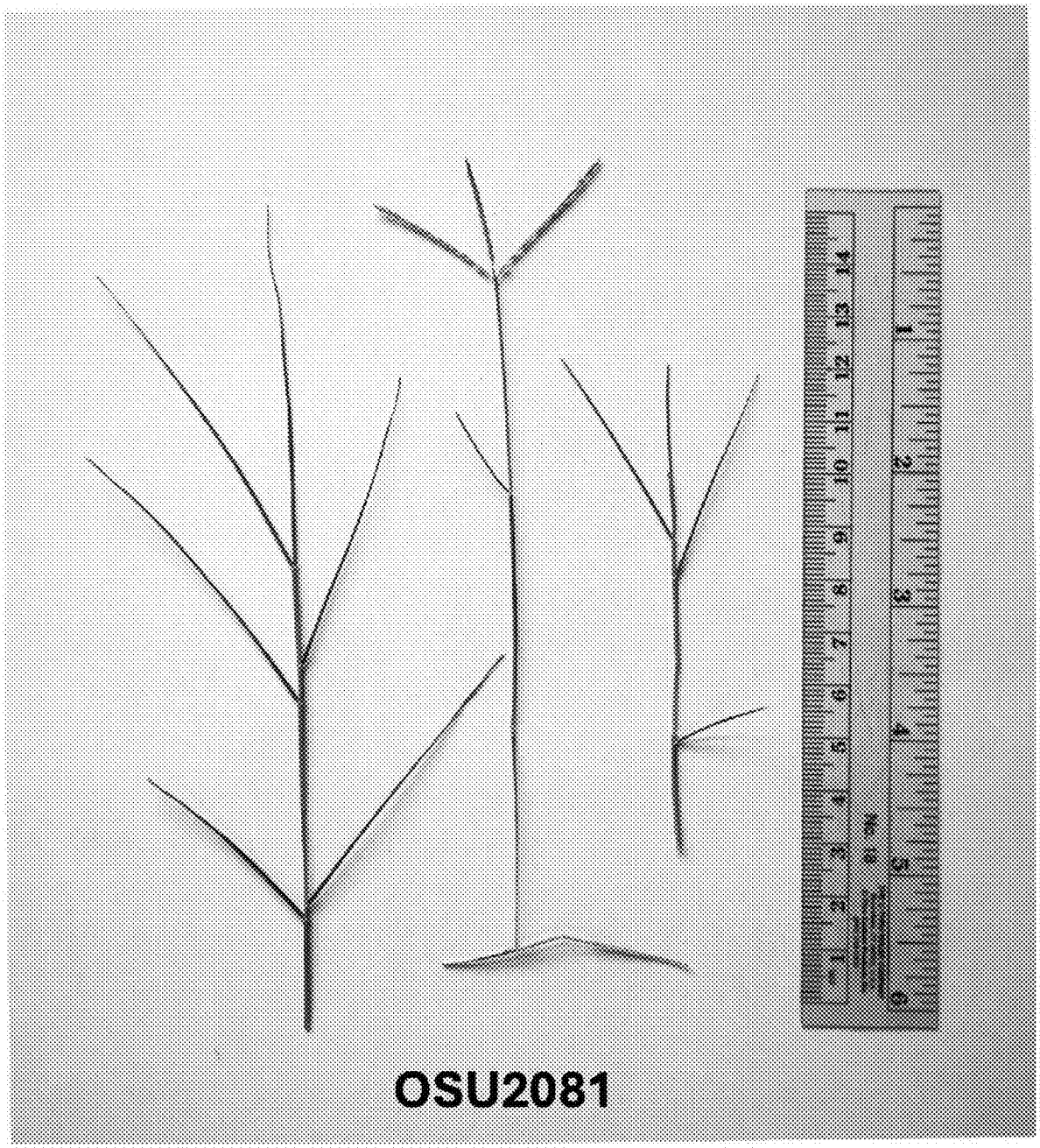
FIG. 3 is a photograph of inflorescences and leaves of bermudagrass variety 'OSU2081' taken on Aug. 6, 2024, at Stillwater, OK of plants one-year old.
Figure 4:
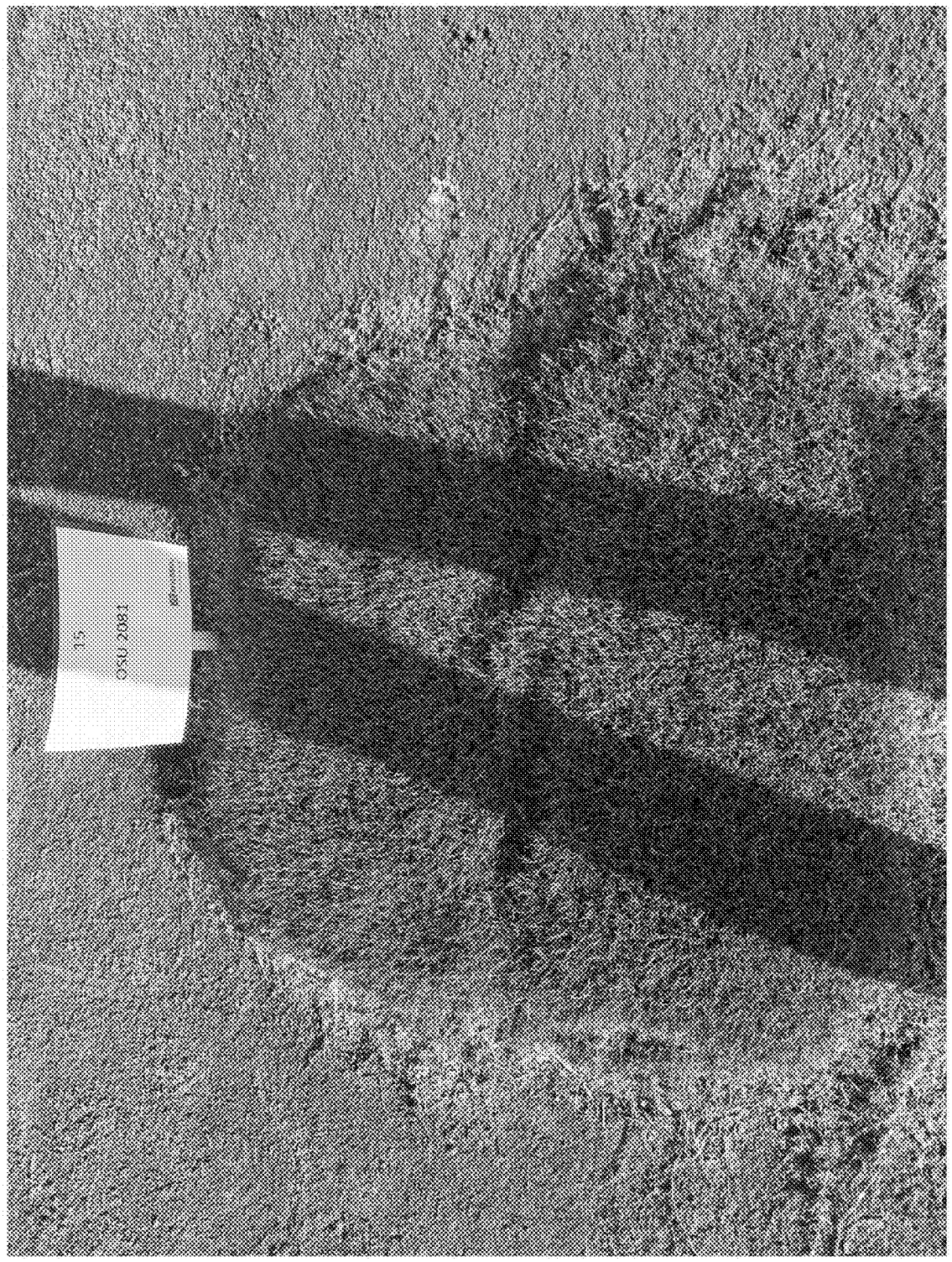
FIG. 4 is a photograph of bermudagrass variety 'OSU2081' taken on Sep. 20, 2022, at Riverside, CA of plants 2-year old under salinity conditions of 4.4 dS $m^{-1}$.
Figure 5:
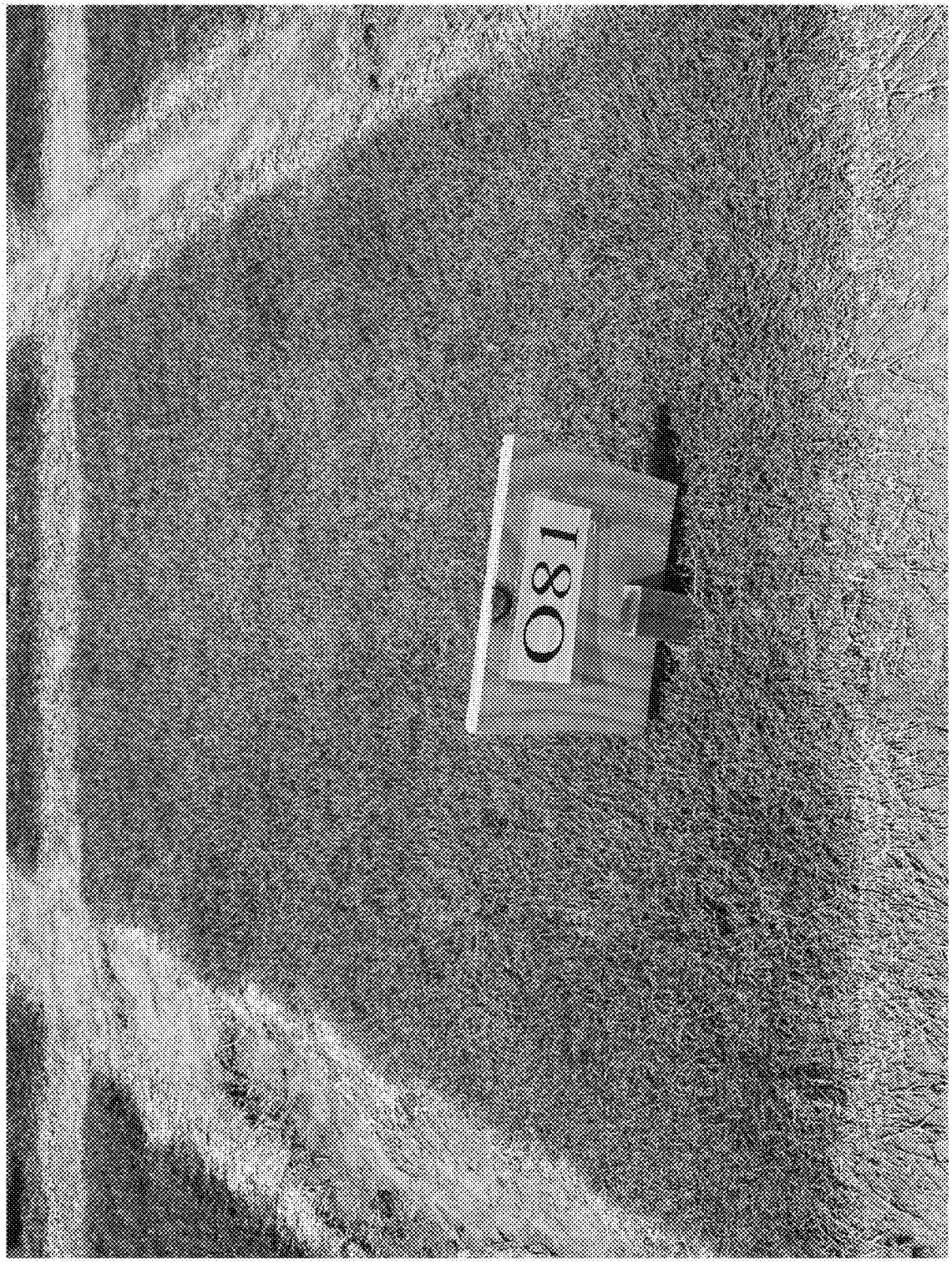
FIG. 5 is a photograph of a plot of 'OSU2081' taken at Stillwater, OK, on May 22, 2022, of 2-year old plants.

Simple sequence repeat (SSR) marker experiments definitively indicated that 'OSU2081' is a unique genotype, distinct from 11 popular cultivars and 20 experimental genotypes tested (FIGS. 1 & 2 listed after REFERENCES).

Morphology Tests

A field trial including five experimental selections ('OSU2081', 'OKC1873' (not patented), 'OKC1682' (not patented), '16x10' (not patented), and 'OSUBF #5' (not patented)), and seven cultivars ('Latitude 36®' (U.S. Plant Pat. No. 24,271), 'NorthBridge®' (U.S. Plant Pat. No. 24,116), 'Patriot' (U.S. Plant Pat. No. 16,801), 'Tahoma 31®' (experimental name 'OKC 1131', U.S. Plant Pat. No. 31,695), 'TifTuf®' (experimental name 'DT-1', U.S. Plant Pat. No. 27,392), 'Tifton10' (not patented), 'Tifway' (not patented), and 'OKC1876' (U.S. Plant Pat. No. 35,548)) was established in 3 replications in a randomized complete block design in Stillwater, Oklahoma in 2021. Twenty stems (subsamples) from each plot were randomly collected in summer 2022. Morphological traits were measured on the subsamples, and plot mean values from subsamples were used in the data analysis. Results indicated that the widths of the first and second leaf blades on the second node of 'OSU2081' were not different from those of 'Latitude 36', 'NorthBridge', 'Tahoma 31', 'TifTuf', 'Tifway', and 'OKC1876', but finer than 'Tifton 10' and 'Patriot' (Table1). The lengths of the two leaf blades of 'OSU2081' were not different from those of 'TifTuf' and 'NorthBridge', but longer than those of the other cultivars. The second internode length of 'OSU2081' was not different from that of 'TifTuf', 'Tifway', and 'OKC1876', but longer than that of the other cultivars. The second internode diameter of 'OSU2081' was finer than that of 'Tifton 10', 'Patriot', and 'NorthBridge', but not different from that of the other cultivars. The raceme number per inflorescence 'OSU2081' was similar to that of 'Latitude 36', 'NorthBridge', 'OKC1876', 'Tahoma 31', 'Tifton 10', and 'Tifway', but smaller than that of 'Patriot' and 'TifTuf'. The raceme length per inflorescence of 'OSU2081' was shorter than that of 'Tifton 10', but not different from other cultivars.

TABLE 1

Morphological measurements of leaf blades, stolons and racemes in turf bermudagrass in a nursery at the Oklahoma State University Turf Research Center in 2022

| Entry | FLW§ | FLL | SLW | SLL | SIL | SID | RN | RL |
|---|---|---|---|---|---|---|---|---|
| 16x10 | 2.03 | 51.00 | 2.03 | 46.50 | 19.87 | 0.87 | 3.6 | 9.87 |
| OKC1682 | 2.00 | 64.40 | 2.00 | 59.47 | 35.27 | 0.73 | 3.1 | 10.17 |
| OKC1873 | 2.03 | 64.23 | 2.10 | 58.93 | 51.97 | 0.60 | 3.0 | 8.80 |
| OKC1876 | 1.83 | 48.80 | 1.83 | 43.77 | 44.23 | 0.50 | 2.8 | 9.27 |
| OSU2081 | 1.97 | 76.30 | 1.97 | 71.47 | 51.50 | 0.50 | 3.1 | 10.57 |
| OSUBF#5 | 2.03 | 47.53 | 2.03 | 44.13 | 28.17 | 0.87 | 3.8 | 11.80 |
| Latitude 36 | 1.80 | 43.93 | 1.80 | 40.23 | 19.10 | 0.67 | 3.0 | 8.17 |
| NorthBridge | 1.97 | 58.90 | 1.97 | 55.33 | 26.33 | 0.77 | 3.0 | 8.90 |
| Patriot | 2.33 | 45.57 | 2.33 | 42.13 | 16.57 | 1.20 | 3.8 | 10.33 |
| Tahoma31 | 1.93 | 46.30 | 1.93 | 42.60 | 21.13 | 0.63 | 3.2 | 7.97 |
| Tifton 10 | 2.87 | 46.17 | 2.87 | 44.23 | 18.00 | 1.63 | 3.4 | 14.67 |
| TifTuf | 2.00 | 73.50 | 2.00 | 66.93 | 53.30 | 0.50 | 3.7 | 12.70 |
| Tifway | 1.97 | 52.50 | 1.97 | 48.47 | 40.07 | 0.53 | 3.2 | 10.47 |
| LSD0.05 | 0.17 | 22.42 | 0.17 | 20.63 | 15.93 | 0.22 | 0.3 | 2.68 |

FLW = $1^{st}$ leaf blade width on $2^{nd}$ node (mm)
FLL = $1^{st}$ leaf blade length on $2^{nd}$ node (mm)
SLW = $2^{nd}$ leaf blade width on $2^{nd}$ node (mm)
SLL = $2^{nd}$ leaf blade length on $2^{nd}$ node (mm)
SIL = $2^{nd}$ internode length (mm)
SID = $2^{nd}$ internode diameter (mm)
RN = raceme number
RL = raceme length (cm)

FLW=$1^{st}$ leaf blade width on $2^{nd}$ node (mm)FLL=$1^{st}$ leaf blade length on $2^{nd}$ node (mm)SLW=$2^{nd}$ leaf blade width on $2^{nd}$ node (mm)SLL=$2^{nd}$ leaf blade length on $2^{nd}$ node (mm) SIL=$2^{nd}$ internode length (mm)SID=$2^{nd}$ internode diameter (mm)RN=raceme number RL=raceme length (cm)

Salinity Tolerance Test

A field experiment to assess bermudagrass response to saline water was conducted at Riverside, CA. The study had 35 experimental entries, including 'OSU2081', and three cultivars ['Santa Ana' (salt tolerant standard) (not patented), 'TifTuf' (drought resistant standard), and 'Tifway' (a widely used commercial standard)]. Plots were planted in the center of 3 ft by 3 ft plots in a randomized complete block design with three replicates in 2020. From 2021 to 2023, the trial was irrigated from July to October (dry season) with saline water (4.4 dS m—1) at 75% reference evapotranspiration (ETO) replacement. Data presented here included experimental entries and the standard cultivars.

When data were averaged across years (Table 2), 'OSU2081' exhibited establishment cover rates (%) better than 'Santa Ana', but no difference from the other two standards. The response of 'OSU2081' to mites (*Eriophyes cynodoniensis*) was similar to the three cultivars. 'OSU2081' was better than 'Tifway' in mite resistance. 'OSU2081' had fall color retention better than 'Tifway', but no difference from 'TifTuf' and 'Santa Ana'. 'OSU2081' produced similar amounts of inflorescence compared to 'Santa Ana', but more inflorescences than 'TifTuf' and 'Tifway' under no saline water irrigation. There is no difference in inflorescence prolificacy among 'OSU2081' and the three standards under saline water irrigation. 'OSU2081''s spring green-up was similar to the three cultivars. 'OSU2081''s turfgrass quality ratings were better than 'Tifway''s under no-saline water irrigation. Under saline water irrigation, 'OSU2081''s turfgrass quality was not different from the three cultivars.

TABLE 2

Turf bermudagrass performance in a saline-water irrigated trial at Riverside, CA for 2020-2023.

| Entry | Cover (%) | Mite Injury& | Fall color | Inflorescence¶ No S¥ | Inflorescence¶ S |
|---|---|---|---|---|---|
| OSU2018 | 70.4 | 5.3 | 5.4 | 4.3 | 3.8 |
| OSU2022 | 92.1 | 5.3 | 6.7 | 2.8 | 4.8 |
| OSU2034 | 88.8 | 6.3 | 6.7 | 1.2 | 3.7 |
| OSU2035 | 84.2 | 7.0 | 6.0 | 4.3 | 3.1 |
| OSU2037 | 53.8 | 6.3 | 2.9 | 1.3 | 3,7 |
| OSU2039 | 50.4 | 5.7 | 5.0 | 3.1 | 3.1 |
| OSU2043 | 87.9 | 4.7 | 6.1 | 5.8 | 3.0 |
| OSU2066 | 90.0 | 8.0 | 6.8 | 6.8 | 2.9 |
| OSU2073 | 91.7 | 5,7 | 7.3 | 7.1 | 3.9 |
| OSU2074 | 75.8 | 6.0 | 1.6 | 2.9 | 3.6 |
| OSU2075 | 93.8 | 4.7 | 4.8 | 7.1 | 3.7 |
| OSU2081 | 93.3 | 6.0 | 7.8 | 5.8 | 2.8 |
| OSU2082 | 98.8 | 6.3 | 7.3 | 5.8 | 3.7 |
| OSU2088 | 81.3 | 6.0 | 6.9 | 7.7 | 3.3 |
| OSU2094 | 97.5 | 4.7 | 5.1 | 7.4 | 3.6 |
| OSU2101 | 93.8 | 5.7 | 6.7 | 5.8 | 4.2 |
| OSU2102 | 65.0 | 4.7 | 5.9 | 3.9 | 3.6 |
| SantaAna | 70.0 | 5.3 | 7.4 | 6.0 | 3.6 |
| TifTuf | 92.9 | 6.3 | 8.1 | 4.2 | 3.4 |
| Tifway | 90.4 | 4.3 | 6.0 | 3.8 | 3.7 |
| LSD0.05 | 9.8 | 1.7 | 1.7 | 1.2 | 2.2 |

| Entry | Recovery | Spring greenup | Turfgrass quality# No S | Turfgrass quality# S |
|---|---|---|---|---|
| OSU2018 | 5.1 | 6.8 | 5.1 | 6.5 |
| OSU2022 | 5.1 | 5.9 | 5.6 | 5.3 |
| OSU2034 | 6.7 | 6.1 | 6.8 | 5.3 |
| OSU2035 | 5.4 | 5.9 | 6.5 | 5.9 |
| OSU2037 | 3.3 | 4.8 | 5.1 | 4.2 |
| OSU2039 | 4.1 | 4.8 | 4.7 | 4.4 |
| OSU2043 | 4.8 | 6.1 | 5.3 | 5.3 |
| OSU2066 | 5.4 | 5.3 | 6.1 | 5.3 |
| OSU2073 | 5.8 | 5.7 | 6.2 | 5.6 |
| OSU2074 | 3.0 | 2.6 | 4.4 | 5.2 |
| OSU2075 | 4.9 | 5.3 | 5.0 | 5.0 |
| OSU2081 | 6.0 | 6.0 | 6.2 | 5.8 |
| OSU2082 | 5.9 | 5.8 | 6.2 | 5.8 |
| OSU2088 | 5.3 | 5.1 | 5.4 | 5.4 |
| OSU2094 | 5.0 | 5.8 | 5.2 | 4.9 |
| OSU2101 | 4.8 | 6.2 | 5.6 | 5.1 |
| OSU2102 | 5.4 | 6.4 | 5.6 | 5.9 |
| SantaAna | 6.7 | 6.7 | 6.2 | 6.0 |
| TifTuf | 6.9 | 6.7 | 6.4 | 6.3 |
| Tifway | 5.3 | 5.3 | 5.4 | 5.8 |
| LSD0.05 | 1.0 | 1.7 | 0.7 | 0.5 |

&Mite injury scale: 1 = 100% damage, 9 = no damage
¶Inflorescence abundance scale: 1 = no seadhead, 9 = maximum abundance
¥No S = no saline water irrigation, S = saline water irrigation
#is a scale, 1 = no wilting, 9 = fully wilting

Regional Drought Resistance Test

This field trial [named Approach C in the 2019-2023 USDA Specialty Crop Research Initiative (SCRI) funded project] was conducted at 8 locations in the southern states (Stillwater, OK; Dallas, TX; Riverside, CA; Tifton and Griffin, GA; Jay and Citra, FL; and Jackson Springs, NC). The test included 34 experimental entries, including 'OSU2081' and three standards ['TifTuf' (drought resistant standard), 'Tahoma 31' (cold hardy, high water-use efficient standard), and 'Tifway' (long-time, widely used standard)].

The nurseries were established using randomized complete block designs with 3 replications in 2020. Once the plots were fully established, the nurseries were not irrigated and managed under natural rainfall conditions. The establishment ratings were collected in 2020 and early 2021, while turf performance data were collected in 2021 to 2023.

'OSU2081' had an average cover (establishment rate %) and leaf spot disease resistance similar to 'TifTuf' and 'Tahoma 31', but higher than 'Tifway' (Table 3). The fall color retention of 'OSU2081' was not different from that of 'TifTuf' and 'Tifway' but was better than 'Tahoma 31'. Under no drought conditions, 'OSU2081' had an inflorescence prolificacy less than 'TifTuf' and 'Tahoma 31' but was not different from 'Tifway'. Under drought conditions, 'OSU2081', 'TifTuf', and 'Tifway' produced similar amounts of seedheads, which were less than 'Tahoma 31'. Under drought conditions, the percent green color (PGC %) estimated from drone images of 'OSU2081' was better than 'Tifway', but similar to 'TifTuf' and 'Tahoma 31'. Under no drought conditions, the average turfgrass quality rating of 'OSU2081' was not different from 'TifTuf' and 'Tahoma 31' but was better than 'Tifway'. Under drought stress, the turfgrass quality of 'OSU2081' was not different from 'TifTuf' but better than 'Tahoma 31' and 'Tifway'. The recovery of 'OSU2081' post drought stress was the same as 'TifTuf', which was better than 'Tahoma 31' and 'Tifway'.

TABLE 3

Turf bermudagrass performance in a field trial at 8 locations in CA, OK, TX, GA, FL, and NC for 2020-2023.

| | | Leaf | | Inflorescences | |
|---|---|---|---|---|---|
| Entry | Cover (%) | spot disease | Fall color | No drought | Drought |
| OSU2015 | 52.8 | 4.7 | 2.6 | 3.6 | 2.7 |
| OSU2018 | 62.2 | 3.3 | 4.1 | 3.4 | 1.7 |
| OSU2021 | 60.9 | 6.0 | 3.0 | 3.4 | 1.0 |
| OSU2022 | 66.9 | 6.7 | 3.6 | 4.4 | 2.7 |
| OSU2026 | 65.0 | 4.0 | 3.9 | 2.8 | 2.0 |
| OSU2034 | 62.5 | 5.0 | 4.0 | 1.1 | 1.0 |
| OSU2035 | 70.6 | 6.3 | 3.9 | 3.7 | 1.0 |
| OSU2037 | 46.1 | 6.0 | 2.7 | 1.4 | 1.0 |
| OSU2039 | 43.9 | 6.0 | 2.5 | 2.2 | 1.0 |
| OSU2043 | 65.0 | 7.3 | 3.7 | 5.1 | 4.0 |
| OSU2066 | 57.2 | 8.0 | 2.6 | 5.7 | 1.0 |
| OSU2073 | 72.1 | 7.7 | 4.7 | 4.3 | 2.0 |
| OSU2074 | 60.3 | 6.0 | 2.1 | 4.4 | 1.7 |
| OSU2075 | 65.3 | 5.3 | 3.2 | 5.1 | 2.3 |
| OSU2081 | 73.6 | 8.7 | 4.8 | 2.5 | 1.3 |
| OSU2082 | 70.5 | 8.3 | 4.3 | 4.5 | 1.7 |
| 0502088 | 67.0 | 6.0 | 4.3 | 5.7 | 3.3 |
| OSU2094 | 67.0 | 8.3 | 2.7 | 4.9 | 6.7 |
| OSU2101 | 59.2 | 8.0 | 3.9 | 6.3 | 4.0 |
| OS02102 | 53.0 | 5.3 | 3.1 | 4.0 | 1.0 |
| Tahoma31 | 69.1 | 7.3 | 3.3 | 3.9 | 6.0 |
| TifTuf | 78.5 | 8.3 | 5.0 | 4.2 | 1.3 |
| Tifway | 62.4 | 5.7 | 4.0 | 2.7 | 1.0 |
| LSD0.05 | 7.5 | 2.6 | 0.8 | 0.9 | 2.2 |

| | | | | Turfgrass quality | |
|---|---|---|---|---|---|
| Entry | PGC(%) Drought | Recovery | Spring greenup | No drought | Drought |
| OSU2015 | 63.4 | 4.8 | 3.9 | 4.8 | 4.1 |
| OSU2018 | 71.1 | 5.1 | 4.9 | 5.6 | 4.8 |
| OSU2021 | 59.9 | 5.0 | 4.5 | 5.0 | 4.1 |
| OSU2022 | 51.9 | 4.7 | 4.5 | 5.0 | 3.7 |
| OSU2026 | 57.3 | 5.1 | 4.4 | 5.2 | 4.1 |
| OSU2034 | 58.9 | 5.2 | 3.7 | 5.2 | 4.1 |
| OSU2035 | 70.2 | 5.3 | 4.0 | 5.4 | 4.6 |
| OSU2037 | 46.5 | 4.2 | 4.3 | 4.7 | 3.3 |
| OSU2039 | 25.2 | 2.7 | 3.4 | 4.2 | 3.1 |
| OSU2043 | 51.1 | 5.0 | 4.2 | 5.2 | 4.3 |
| OSU2066 | 45.2 | 3.8 | 2.4 | 4.0 | 3.3 |
| OSU2073 | 94.8 | 6.2 | 4.5 | 5.9 | 5.7 |
| OSU2074 | 82.6 | 4.9 | 2.3 | 4.8 | 4.5 |
| OSU2075 | 88.6 | 5.4 | 4.1 | 5.1 | 4.8 |
| OSU2081 | 92.8 | 6.1 | 4.6 | 5.9 | 5.6 |
| OSU2082 | 94.9 | 5.9 | 4.3 | 5.6 | 5.6 |
| 0502088 | 81.1 | 5.6 | 4.5 | 5.3 | 4.9 |
| OSU2094 | 90.1 | 5.1 | 4.2 | 5.0 | 4.9 |
| OSU2101 | 58.3 | 3.9 | 4.6 | 5.5 | 4.6 |
| OS02102 | 43.4 | 4.4 | 4.0 | 5.1 | 3.9 |
| Tahoma31 | 85.7 | 5.2 | 5.4 | 5.7 | 5.0 |
| TifTuf | 89.9 | 6.1 | 5.3 | 6.1 | 5.8 |
| Tifway | 53.1 | 5.0 | 4.3 | 5.6 | 4.7 |
| LSD0.05 | 12.8 | 0.5 | 0.8 | 0.2 | 0.3 |

Shade Tolerance Test

Approximately 40 bermudagrasses were evaluated at two locations (Stillwater, OK and College Station, TX) over four years (2020-2023). Grasses were planted as plugs in mid-July 2020 in Stillwater and mid-August in College Station. Shade was applied in the form of a neutral density poly woven fabric nominally rated to reduce irradiance by 50% (Stillwater) or 63% (College Station) beginning 3 weeks after planting (Stillwater) or 10 weeks after planting (College Station). Turfgrass quality and green coverage were measured monthly during the growing season in 2021-2023 to assess the spread and persistence of plant materials under shade. Data pooled across locations and years indicated 'Tahoma31' (shade tolerant standard) was the best-performing commercial standard, resulting in a mean quality score of 5.0, while 'OSU2081' was considered less well-adapted to shade, although comparable to other bermudagrasses in the trial (Table 4). Results suggest that 'OSU2081' would perform better than 'Tifway' (shade susceptible standard) under shaded conditions.

TABLE 4

Performance of selected bermudagrasses in the SCRI ancillary trait shade trial conducted in Stillwater, OK and College Station, TX from 2020 to 2023.

| Entry | Cover (%) | Spring green up | Turfgrass quality |
|---|---|---|---|
| OSU2015 | 46.8 | 2.5 | 3.9 |
| OSU2018 | 41.0 | 3.2 | 3.8 |
| OSU2021 | 60.1 | 3.2 | 5.4 |
| OSU2022 | 46.3 | 2.8 | 3.9 |
| OSU2026 | 40.8 | 2.2 | 3.4 |
| OSU2034 | 43.4 | 2.8 | 3.8 |
| OSU2035 | 40.1 | 2.7 | 2.9 |
| OSU2037 | 46.0 | 3.7 | 4.1 |
| OSU2039 | 36.9 | 3.2 | 2.5 |
| OSU2043 | 42.3 | 3.2 | 3.3 |
| OSU2066 | 37.9 | 2.6 | 3.2 |
| OSU2073 | 40.9 | 3.0 | 3.8 |
| OSU2074 | 35.0 | 2.2 | 2.7 |
| OSU2075 | 38.9 | 2.7 | 3.3 |
| OSU2081 | 46.3 | 3.2 | 4.4 |
| OSU2082 | 38.4 | 2.3 | 3.0 |
| OSU2088 | 41.5 | 2.3 | 3.7 |
| OSU2094 | 38.6 | 2.8 | 3.2 |
| OSU2101 | 38.6 | 1.7 | 3.1 |
| OSU2102 | 35.3 | 2.3 | 2.6 |
| Tahoma31 | 48.6 | 3.3 | 5.0 |
| Tifway | 38.4 | 2.3 | 3.1 |
| LSD 0.05 | 7.2 | 1.3 | 0.4 |

Sod Harvestability Test

Approximately 40 bermudagrasses were evaluated in Stillwater, OK from 2021 to 2022. Grasses were planted 8 Jul. 2021 from sprigs at 450 bu/acre. Spring green-up and green coverage were measured the year after planting to assess spread. Sod was harvested using a walk behind sod cutter fitted with an 18-inch blade and 1.5-inch depth setting. Sod tensile strength was measured using the device described by Segars et al. (2022) in the horizontal orientation and a digital force meter (Chatillon brand, digital force instrument, Model DFIS, John Chatillon & Sons, Inc., Greensboro, NC) operated in peak weight model to determine the maximum force at the time of tearing. Raw data were converted using the sod pad width and depth information to reflect the point of sod tensile failure per unit area (kg dm—2). Sod handling quality was assessed on a 1 to 5 visual scale where 1 =very poor quality, sod falls apart easily, 2 =substantial cracking of sod strip, 3 =some cracking of sod pad, this is the suggested minimum quality for harvest of an existing commercial available product, 4 =very little cracking, suggested minimum quality for commercialization of new experimental varieties, 5 =excellent quality, no cracking of pad (Han, 2009). Data indicate that 'Tahoma 31' and 'TifTuf' had better spring green-up than 'OSU 2081'; however, each genotype grew well and filled in the block at the rating time (Table 5). Sod tensile strength was acceptable for each genotype at 12 months after planting, although sod handling quality varied with 'OSU 2081' having inferior quality than 'Tahoma 31'.

Table 5. Summary results of selected entries from SCRI sod strength trial in Stillwater, OK.

TABLE 5

Summary results of selected entries from SCRI sod strength trial in Stillwater, OK.

| | Spring Green Up 11 Apr. 2022 1 to 9 | Green Cover 7 Jun. 2022 % | Sod Tensile Strength 14 Jul. 2022 kg $dm^{-2}$ | Sod Handling Quality 14 Jul. 2022 1 to 5 | Sod Tensile Strength 6 Oct. 2022 kg $dm^{-2}$ | Sod Handling Quality 6 Oct. 2022 1 to 5 |
|---|---|---|---|---|---|---|
| OSU2021 | 5.0b | 70b | 15.1b | 2.7bc | 19.5a | 5.0a |
| OSU2073 | 4.0b | 99a | 27.8ab | 3.0ab | 19.3a | 4.7a |
| OSU2081 | 2.3c | 94a | 34.2a | 2.0c | 15.2ab | 4.7a |
| OSU2082 | 2.7c | 98a | 13.7b | 2.3bc | 7.7b | 4.7a |
| Tahoma 31 | 7.3a | 99a | 20.8ab | 3.7a | 16.7a | 5.0a |
| TifTuf | 6.7a | 99a | 18.3ab | 2.7bc | 10.7ab | 5.0a |

Sod Harvestability on Farm Tests

'OSU2081' was planted in an approximately 20' by 20' plot in Arcadia, FL in fall 2021. The plot was harvested with a KWMI sod harvester on Jun. 14, 2022. The harvest showed that 'OSU2081' had excellent harvestability in the sandy soil. In addition, 'OSU2081' was planted in Yukon, OK in summer 2023. In early December 2023,'OSU2081' exhibited adequate sod strength despite the stands being young (observed by the sod farmer). But 'OSU2081' sod harvestability was not as good as 'Tahoma 31'. The sod farmer indicated that the 'OSU2081' plot was in a lower area and had not grown as thick as 'Tahoma 31' in the growing season.

Shared Space Planted Nursery (SSPN) Test

This regional field trial was carried out at 7 locations in the southern states (Stillwater, OK; Dallas, TX; Riverside, CA; Tifton and Griffin, GA; Citra, FL; and Jackson Springs, NC). The test included 190 experimental entries ('OSU2081' included) and three standards ('TifTuf', 'Tahoma 31', and 'Tifway'). The nurseries were established using randomized complete block designs with 2 replications in 2020. After the plots were fully established, the nurseries were not irrigated and managed under natural rainfall conditions. The establishment ratings were collected in 2020 and early 2021, while turf performance data were collected from 2021 to 2023. Data analysis results include selected experimental entries and standard cultivars are presented in Table 6.

'OSU2081' grew as fast as the three standard cultivars in the establishment stage. Its fall color rating was as good as that of 'TifTuf', which was better than that of 'Tahoma 31' and 'Tifway'. 'OSU2081' and the three cultivars were not different in inflorescence prolificacy and spring green up. Under drought conditions, the PGC (%) of 'OSU2081' was similar to that of 'TifTuf' and 'Tahoma 31', but better than 'Tifway'. Under no drought stress, 'OSU2081' had a turfgrass quality rating similar to 'TifTuf', but better than 'Tahoma 31' and 'Tifway'. Under drought stress conditions, 'OSU2081' was the top performer for turfgrass quality better than 'Tahoma 31' and 'Tifway', although not different from 'TifTuf'.

TABLE 6

Turfgrass performance of OSU experimental selections and three commercial cultivars at seven locations over four years (2020-2023).

| Entry | Cover (%) | Fall color | Inflorescences No drought | PGC(%) Drought |
|---|---|---|---|---|
| OSU2035 | 47.0 | 4.0 | 3.6 | 64.6 |
| OSU2050 | 46.2 | 4.4 | 2.5 | 52.1 |
| OSU2052 | 45.4 | 4.1 | 2.6 | 43.7 |
| OSU2053 | 55.9 | 4,9 | 3.8 | 78.6 |
| OSU2055 | 38.1 | 3.0 | 2.0 | 48.6 |
| OSU2056 | 44.3 | 3.6 | 4.5 | 54.2 |
| OSU2061 | 40.7 | 1.9 | 2.0 | 37.2 |
| OSU2069 | 56.5 | 4.1 | 3.2 | 55.5 |
| OSU2071 | 42.9 | 3.0 | 5.0 | 35.1 |
| OSU2072 | 51.4 | 3.8 | 5.3 | 74.3 |
| OSU2077 | 51.2 | 5.0 | 2.0 | 68.0 |
| OSU2079 | 54.8 | 4.5 | 2.6 | 63.9 |
| OSU2081 | 57.6 | 5.6 | 2.6 | 69.9 |
| OSU2082 | 56.2 | 4.5 | 3.4 | 55.7 |
| OSU2085 | 43.4 | 1.9 | 1.7 | 48.3 |
| OSU2087 | 49.4 | 5.0 | 3.6 | 77.5 |
| OSU2090 | 47.5 | 3.2 | 4.1 | 54.9 |
| OSU2093 | 50.6 | 3.7 | 4.5 | 56.8 |
| OSU2100 | 45.4 | 4.3 | 2.9 | 72.8 |
| Tahoma31 | 50.4 | 3.0 | 3.7 | 65.3 |
| TifTuf | 66.8 | 5.6 | 4.1 | 81.0 |
| Tifway | 49.9 | 3.6 | 3.4 | 42.6 |
| LSD0.05 | 10.6 | 0.9 | 1.8 | 12.4 |

| Entry | Recovery | Spring greenup | Turfgrass quality No drought | Turfgrass quality Drought |
|---|---|---|---|---|
| OSU2035 | 5.4 | 4.6 | 5.4 | 4.5 |
| OSU2050 | 6.0 | 4.2 | 5.2 | 4.6 |
| OSU2052 | 5.0 | 4.2 | 5.2 | 4.5 |
| OSU2053 | 5.9 | 4.8 | 5.6 | 5.0 |
| OSU2055 | 6.3 | 2.7 | 5.5 | 5.3 |
| OSU2056 | 5.3 | 3.9 | 5.2 | 4.3 |
| OSU2061 | 5.4 | 2.2 | 4.8 | 4.6 |
| OSU2069 | 5.9 | 4.3 | 5.5 | 5.0 |
| OSU2071 | 5.7 | 3.7 | 4.8 | 4.8 |
| OSU2072 | 5.3 | 3.3 | 5.1 | 4.4 |
| OSU2077 | 5.9 | 4.4 | 5.8 | 5.2 |
| OSU2079 | 5.9 | 4.3 | 5.7 | 5.0 |
| OSU2081 | 6.5 | 4.9 | 6.2 | 5.7 |
| OSU2082 | 5.2 | 4.0 | 5.4 | 4.6 |
| OSU2085 | 5.0 | 2.3 | 4.3 | 4.0 |
| OSU2087 | 5.9 | 4.2 | 5.5 | 4.6 |
| OSU2090 | 5.4 | 3.5 | 4.9 | 4.3 |
| OSU2093 | 5.6 | 4.1 | 5.1 | 4.3 |
| OSU2100 | 5.5 | 4.4 | 5.1 | 4.5 |
| Tahoma31 | 5.1 | 5.3 | 5.8 | 4.2 |
| TifTuf | 5.9 | 5.1 | 6.3 | 5.8 |
| Tifway | 5.0 | 4.3 | 5.1 | 3.8 |
| LSD0.05 | 0.8 | 1.0 | 0.3 | 0.5 |

What is claimed is:

1. A new and distinct Bermudagrass plant variety OSU2081 substantially as described and illustrated herein.

* * * * *